United States Patent [19]
Smith

[11] Patent Number: 6,166,049
[45] Date of Patent: Dec. 26, 2000

[54] USE OF AN ANTAGONIST OF PPARα AND PPARγ FOR THE TREATMENT OF SYNDROME X

[75] Inventor: Stephen Alistair Smith, Bramfield, United Kingdom

[73] Assignee: SmithKline Beecham P.L.C., United Kingdom

[21] Appl. No.: 09/101,316

[22] PCT Filed: Jan. 7, 1997

[86] PCT No.: PCT/EP97/00058

§ 371 Date: Sep. 10, 1998

§ 102(e) Date: Sep. 10, 1998

[87] PCT Pub. No.: WO97/25042

PCT Pub. Date: Jul. 17, 1997

[30] Foreign Application Priority Data

Jan. 9, 1996 [GB] United Kingdom .................. 9600464

[51] Int. Cl.$^7$ ........................... A61K 31/44; A61K 31/42
[52] U.S. Cl. ........................... 514/352; 514/375; 514/866
[58] Field of Search .................................... 514/352, 375, 514/866

[56] References Cited

U.S. PATENT DOCUMENTS 5,130,333  7/1992  Pan et al. ................................ 514/460

FOREIGN PATENT DOCUMENTS

| 0 302 481 A2 | 2/1989 | European Pat. Off. | ........ A61K 31/20 |
| WO 94/01420 | 1/1994 | WIPO | ........... C07D 263/58 |
| WO 96/04260 | 2/1996 | WIPO | ........... C07D 263/58 |
| WO 96/04261 | 2/1996 | WIPO | ........... C07D 263/58 |

OTHER PUBLICATIONS

S. Csögör and P. Bornemisza, "The Effect of Clofibrate (Atromid) on Intravenous Tolbutamide, Oral and Intravenous Glucose Tolerance Tests", *Clinical Trials Journal*, vol. 14, No. 1, pp. 15–22 (1977).

Dreyer et al., "Positive Regulation of the Peroxisomal β–oxidation Pathway by Fatty Acids Through Activation of Peroxisome Proliferator–activated Receptors (PPAR)", *Biol. Cell*, vol. 77, pp. 67–76 (1993).

Enger et al., "The Effect of Clofibrate on Glucose Tolerance, Insulin Secretion, Triglycerides and Fibrinogen in Patients with Coronary Heart Disease", *Acta Med. Scand.*, vol. 201, pp. 563–566 (1977).

J. Karam, "Type II Diabetes and Syndrom X", *Endocrinology and Metabolism Clinics of North America*, vol. 21, No. 2, pp. 329–350 (1992).

Kliewer et al., "A Prostaglandin $J_2$ Metabolite Binds Peroxisome Proliferator–Activated Receptor γ and Promotes Adipocyte Differentiation", *Cell*, vol. 83, pp. 813–819 (1995).

Lehmann et al., "An Antidiabetic Thiazolidinedione Is a High Affinity Ligand for Peroxisome Proliferator–activated Receptor γ (PPARγ)", *The Journal of Biological Chemistry*, vol. 270, No. 22, pp. 12953–12956 (1995).

Tontonoz et al., "Stimulation of Adipogenesis in Fibroblasts by PPARγ2 a Lipid–Activated Transcription Factor", *Cell*, vol. 79, pp. 1147–1156 (1994).

Willson et al., "The Structure–Activity Relationship between Peroxisome Proliferator–Activated Receptor γ Agonism and the Antihyperglycemic Activity of Thiazolidinediones", *J. Med. Chem.*, vol. 39, pp. 665–668 (1996).

*Primary Examiner*—Kimberly Jordan
*Attorney, Agent, or Firm*—Kirk Baumeister; William T. King

[57] ABSTRACT

A method for the treatment or prophylaxis of Syndrome X in a human or non-human mammal is disclosed. The method comprises the administration of an effective, non-toxic and pharmaceutically effective amount of an agonist of PPARα and PPARγ, or a pharmaceutically acceptable derivative thereof, to a human or non-human mammal in need thereof.

5 Claims, No Drawings

USE OF AN ANTAGONIST OF PPARα AND PPARγ FOR THE TREATMENT OF SYNDROME X

This application is a 371 of PCT/EP97/00358, filed Jan. 7, 1997.

This invention relates to a novel method of treatment, in particular for the treatment of Syndrome X and certain compounds used in said method.

It is known that the γ-isoform of peroxisome proliferator-activated receptor (herein after PPARγ) is member of a nuclear receptor superfamily that includes receptors for the steroid, thyroid and retinoid hormones(Evans, Science 240, 889–895, (1988)). It is also known from Chawla et al that PPARγ is expressed early during the differentiation of adipocytes (Endocrinology 135,798–800, 1994).

Spiegelman et al state in Cell (Vol 83, 803–812, 1995) that signals which modulate PPARγ activity may serve a primary role in regulating energy homeostasis. They conclude (ibid, 810) that 'screening for potent PPARγ agonists and antagonists represents a logical and potentially rapid approach towards the development of novel therapeutic agents for NIDDM and obesity respectively.'.

It is known that the α-isoform of peroxisome proliferator-activated receptor (herein after PPARα) acts to stimulate peroxisomal proliferation in the rodent liver which leads to enhanced fatty oxidation by this organ (Keller and Wahli: Trends Endocrin Metab 1993;4:291–296). Hypolipidaemic agents have the ability to stimulate PPAR alpha and the ensuing stimulation of peroxisomal proliferation and consequent fatty acid oxidation can account for the reduction in plasma fatty acids (Macdonald and Lane: Current Biology Vol5 pp618–621 (1995)).

Syndrome X is the syndrome characterised by an initial insulin resistant state, generating hyperinsulinaemia, dyslipidaemia and impaired glucose tolerance, which can progress to non-insulin dependent diabetes mellitus (Type II diabetes), characterised by hyperglycaemia and which then further progresses to diabetic complications.

We now consider that inclusion of PPARα effects in a PPARγ antihyperglycaemic agent will result in a reagent with enhanced therapeutic potential in the syndrome X aetiology due to an enhanced hypolipidaemic effect.

International Patent Application number PCT/EP 95/03038 discloses certain compounds of formula (A):

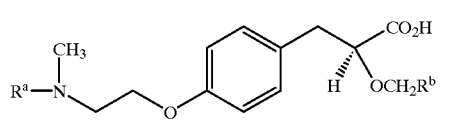

(A)

or a pharmaceutically acceptable salt thereof, and/or a pharmaceutically acceptable solvate thereof, wherein $R^a$ represents 2-benzoxazolyl or 2-pyridyl and $R^b$ represents $CH_2OCH_3$ or $CF_3$.

The compounds of formula (A) are stated to be of potential use in the treatment and/or prophylaxis of hyperglycaemia, especially in Type II diabetes, hyperlipidaemia, hypertension, cardiovascular disease, especially atherosclerosis and of renal disease, especially renal disease associated with the development of Type II diabetes including diabetic nephropathy, glomerulonephritis, glomerular sclerosis, nephrotic syndrome, hypertensive nephrosclerosis and end stage renal disease and for the prevention, reversal, stabilisation or retardation of the progression of microalbuminuria to albuminuria.

It has now been discovered that the compounds of formula (A) exhibit agonist activity at both PPARα and PPARγ and that as well as being particularly effective for the treatment and/or prophylaxis of hyperglycaemia they are also now considered to be most effective for the treatment and/or prophylaxis of pre-diabetic insulin resistance syndrome and the resulting complications thereof: They are therefore considered to be useful for the treatment and/or prophylaxis of insulin resistance, diabetes, dyslipidaemia, atherosclerosis, hypertension, cardiovascular disease and obesity.

Accordingly, in a first aspect the invention provides a method for the treatment and/or prophylaxis of Syndrome X in a human or non-human mammal, which method comprises the administration of an effective, non-toxic and pharmaceutically effective amount of an agonist of PPARα and PPARγ, or a pharmaceutically acceptable derivative thereof, to a human or non-human mammal in need of such treatment.

Thus, one aspect of the invention is the treatment of Syndrome X.

A further aspect of the invention is the prophylaxis of Syndrome X.

In particular, there is provided a method for the treatment and/or prophylaxis of hyperglycaemia.

In particular there is provided a method for the treatment of pre-diabetic insulin resistance syndrome and the resulting complications thereof.

Pre-diabetic insulin resistance syndrome includes hyperinsulinaemia and impaired glucose tolerance.

In a further aspect, there is provided a method for the treatment and/or prophylaxis of Syndrome X, including hyperglycaemia and/or pre-diabetic insulin resistance syndrome and the resulting complications thereof, in a human or non-human mammal, which method comprises the administration of an effective, non-toxic and pharmaceutically effective amount of an agonist of PPARα and PPARγ, or a pharmaceutically acceptable derivative thereof, to a human or non-human mammal in need thereof; providing the method does not include the administration of:

(S)-3-[4-[2-[N-(2-benzoxazolyl)-N-methylamino]ethoxy]phenyl]-2-(2-methoxyethoxy)propanoic acid; or (S)-3-[4-[2- [N-(2-benzoxazolyl)-N-methylamino]ethoxy]phenyl]-2-(2,2,2-trifluoroethoxy)propanoic acid, for the treatment and/or prophylaxis of: hyperglycaemia, especially in Type II diabetes, hyperlipidaemia, hypertension, cardiovascular disease, especially atherosclerosis and of renal disease, especially renal disease associated with the development of Type II diabetes including diabetic nephropathy, glomerulonephritis, glomerular sclerosis, nephrotic syndrome, hypertensive nephrosclerosis and end stage renal disease and for the prevention, reversal, stabilisation or retardation of the progression of microalbuminuria to albuminuria.

It will be appreciated that in its preferred form the agonist of PPARα and PPARγ is a single compound (such compound being referred to herein as a 'PPARα and γ agonist') but it is within the ambit of this invention that the agonist of PPARα and PPARγ is provided by a combination of a PPARα agonist compound and a PPARγ agonist compound.

One combined PPARα and γ agonist is a compound of formula (I):

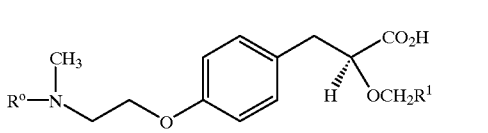

or a pharmaceutically acceptable salt thereof, and/or a pharmaceutically acceptable solvate thereof, wherein $R^0$ represents 2-benzoxazolyl or 2-pyridyl and $R^1$ represents $CH_2OCH_3$ or $CF_3$.

Preferably, $R^0$ represents 2-benzoxazolyl.
Suitably, $R^1$ represents $CH_2OCH_3$.
Preferably, $R^1$ represents $CF_3$.

The compounds of formula (I), and the pharmaceutically acceptable salts thereof, may exist in one of several tautomeric forms, all of which are encompassed by the present invention as individual tautomeric forms or as mixtures thereof.

Pharmaceutically acceptable derivatives include pharmaceutically acceptable salts and solvates.

Suitable pharmaceutically acceptable salts include salts of carboxy groups and acid addition salts.

Suitable pharmaceutically acceptable salts of carboxy groups include metal salts, such as for example aluminium, alkali metal salts such as lithium, sodium or potassium, alkaline earth metal salts such as calcium or magnesium and ammonium or substituted ammonium salts, for example those with lower alkylamines such as triethylamine, hydroxy alkylamines such as 2-hydroxyethylamine, bis-(2-hydroxyethyl)amine or tri-(2-hydroxyethyl)amine, cycloalkylamines such as bicyclohexylamine, or with procaine, dibenzylpiperidine, N-benzyl-β-phenethylamine, dehydroabietylamine, N,N'-bisdehydroabietylamine, glucamine, N-methylglucamine or bases of the pyridine type such as pyridine, collidine, quinine or quinoline.

Suitable acid addition salts include pharmaceutically acceptable inorganic salts such as the sulphate, nitrate, phosphate, borate, hydrochloride and hydrobromide and, where feasible, pharmaceutically acceptable organic acid addition salts such as acetate, tartrate, maleate, citrate, succinate, benzoate, ascorbate, methanesulphonate, α-keto glutarate and α-glycerophosphate.

Suitable pharmaceutically acceptable solvates include hydrates.

The pharmaceutically acceptable derivatives, such as the salts and/or solvates of the compounds of formula (I) may be prepared and isolated according to conventional procedures, for example sodium salts may be prepared by using sodium methoxide in methanol.

A compound of formula (I), or a pharmaceutically acceptable salt thereof, and/or a pharmaceutically acceptable hydrate thereof, may be prepared by hydrolysing a compound of formula (II):

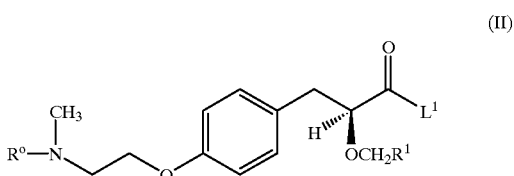

wherein $R^0$ and $R^1$ are as defined in relation to formula (I) and $L^1$ represents a hydrolysable group; and thereafter, if required, preparing a pharmaceutically acceptable salt of the compound of formula (I) and/or a pharmaceutically acceptable solvate thereof.

A suitable hydrolysable group $L^1$ is a group of formula (a) or an epimer thereof:

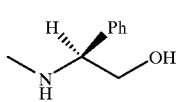

A suitable hydrolysable group $L^1$ is an Evans chiral auxiliary, for example a group of formula (b) or an epimer thereof:

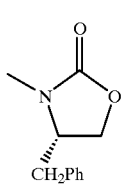

A suitable hydrolysable group $L^1$ is a $C_{1-6}$ alkoxy group.

The hydrolysis of the compound of formula (II) is carried out using conditions appropriate for hydrolysing the particular group $L^1$ chosen, for example when $L^1$ is a group of formula (a) or a $C_{1-6}$ alkoxy group, the hydrolysis is suitably carried out under acidic conditions, for example using dilute sulphuric acid, conveniently in a water/dioxan mixture, for example a 1:1 mixture, at any temperature which provides a suitable rate of formation of the required product, generally at an elevated temperature, such as in the range of from 50° C. to 120° C., for example 90° C.; or when $L^1$ is a group of formula (b) the hydrolysis is generally carried out using lithium hydroperoxide in an aqueous solvent, such as aqueous tetrahydrofuran, at any temperature which provides a suitable rate of formation of the required product, generally at a reduced temperature, such as in the range of from −10° C. to 0° C., for example 0° C. Alternatively, when $L^1$ is a group of formula (b) the hydrolysis may be effected under basic conditions, using for example aqueous sodium hydroxide, in an appropriate solvent such as aqueous tetrahydrofuran usually at ambient temperature.

A compound of formula (II), wherein $L^1$ is a moiety of the above defined formula (a) or (b), may be prepared from a compound of formula (III):

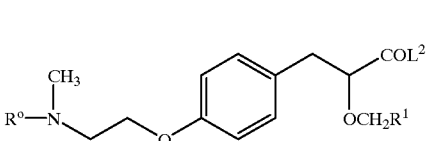

wherein $R^0$ and $R^1$ are as defined in relation to formula (I) and $L^2$ represents a leaving group; (i) for compounds of formula (II) wherein $L^1$ is a moiety of the above defined formula (a), by reaction with (S)-phenylglycinol; or (ii) for compounds of formula (II) wherein $L^1$ is a moiety of the above defined formula (b), by reaction with (S)-4-benzyloxazolidin-2-one, preferably an activated form thereof; and thereafter separating the required isomer from the mixture of diastereoisomers produced.

A suitable leaving group $L^2$ is a halogen atom, for example a chlorine atom.

The reaction between the compounds of formula (III) and (S)-phenylglycinol may be carried out under conventional amidation conditions, for example in an inert solvent such as dichloromethane at a temperature which provides a suitable rate of formation of the required product, suitably at ambient temperature and preferably in the presence of a base such as triethylamine.

A suitable activated form of (S)-4-benzyloxazolidin-2-one is a salted form, for example an alkali metal salted form, preferably a lithium salt.

The activated form of (S)-4-benzyloxazolidin-2-one may be prepared by any appropiate conventional method. Thus when the activated form is a lithium salt, it may be prepared by treating (S)-4-benzyloxazolidin-2-one with a source of lithium ions in the presence of a base, suitably provided by n-butyllithium, in an aprotic solvent such as tetrahydrofuran, usually at a low temperature, for example in the range of from −78° to 0° C.

The reaction between the compound of formula (III) and the activated form of (S)-4-benzyloxazolidin-2-one may be carried out in an aprotic solvent, such as tetrahydrofuran, at a temperature which provides a suitable rate of formation of the required product, conveniently by allowing the reaction mixture to slowly warm from −78° to 0° C.

Preferably, the activated form of (S)-4-benxyloxazolidin-2-one is prepared and then reacted in-situ with the compound of formula (III).

A compound of formula (III) may be prepared by hydrolysing the carboxylic ester COOR$^2$ of a compound of formula (IV):

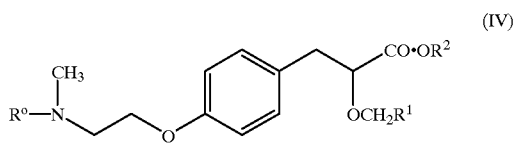

wherein R$^0$ and R$^1$ are as defined in relation to formula (I) and R$^2$ represents an alkyl group, and thereafter converting the carboxylic acid group so formed into a moiety CO.L$^2$.

A suitable alkyl group R$^2$ is a C$_{1-6}$ alkyl group, especially a methyl group.

The hydrolysis of the carboxylic ester may be effected by use of any conventional hydrolysing agent, such as an alkaline metal hydroxide, for example sodium hydroxide.

The hydrolysis of the compound of formula (IV) may be carried out in any suitable solvent such as a methanol/water mixture, conveniently a 1:1 mixture, at a temperature which provides a suitable rate of formation of the required product, suitably at an elevated temperature and conveniently at the reflux temperature of the solvent.

The conversion of the carboxylic acid group into the moiety CO.L$^2$ may be carried out using any appropiate conventional procedure, depending upon the particular nature of the group L$^2$ chosen, thus when L$^2$ is a halogen a suitable procedure involves treatment of the carboxylic acid with an oxalyl halide, for example oxalyl chloride when L$^2$ is chlorine.

The reaction conditions for the conversion of the carboxylic acid group into the moiety CO.L$^2$ will be dictated by the particular nature of L$^2$ and the source of L$^2$ chosen, for example when L$^2$ is halogen and the source of L$^2$ is oxalyl chloride then the reaction may be carried out in an inert solvent such as dichloromethane or benzene at a temperature which provides a suitable rate of formation of the required product, suitably at ambient temperature or at an elevated temperature such as the reflux temperature of the solvent.

It will be appreciated that the preparation and separation of a compound of formula (II) wherein L$^1$ is an epimer of the above defined moiety (a) or (b) and its subsequent hydrolysis to afford a compound of formula (I) can be achieved by employing analogous methods to those described above for the preparation, separation and hydrolysis of a compound of formula (II) wherein L$^1$ represents the above defined moiety (a) or (b).

A compound of formula (II) wherein L$^1$ is a moiety of formula (b) may also be prepared by dehydroxylation of a compound of formula (V):

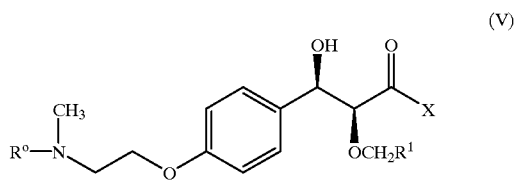

wherein R$^0$ and R$^1$ are as defined in relation to formula (I) and X is a moiety of the above defined formula (b).

The dehydroxylation of the compound of formula (V) is conveniently carried out by treatment with a trialkylsilane, for example triethylsilane, preferably in the presence of trifluoroacetic acid and conveniently using trifluoroacetic acid as solvent, at any temperature providing a suitable rate of formulation of the product, for example at a temperature in the range from 0° C. to room temperature.

It will be appreciated that a compound of formula (II) wherein L$^1$ is a moiety of formula (b) would also be obtained by dehydroxylation of a compound of formula (V) in which the hydroxy bearing stereocentre is epimerised.

A compound of formula (V) may be prepared by reacting a compound of formula (VIA):

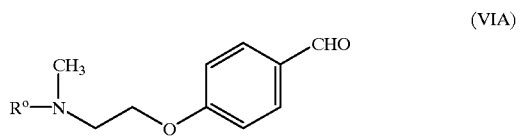

wherein R$^0$ is as defined in relation to formula (I), with a compound of formula (VIB):

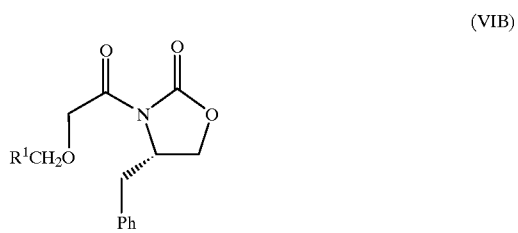

wherein R$^1$ is as defined in relation to formula (I); and thereafter separating the required isomer from the mixture of diastereoisomers produced.

Suitably in the above mentioned reaction, the compound of formula (VIB) is in an activated form, which is preferably provided by treating the compound of formula (VIB) with an alkylboron triflate, for example dibutylboron triflate, preferably in the presence of an amine base such as triethylamine.

The activated form of the compound of formula (VIB) may be prepared by the appropriate conventional method depending upon the specific nature of the activated form chosen, for example the compound of formula (VIB) is reacted with dibutylboron triflate and triethylamine in an inert solvent such as dichloromethane at a temperature in the range of from −78° to 0° C.

The reaction between the compounds of formulae (VIA) and (VIB) may be carried out in an in an inert solvent such as dichloromethane, at a temperature which provides a suitable rate of formation of the required product, conveniently by allowing the reaction mixture to slowly warm from −78° to 0° C.

Preferably, the activated form of the compound of formula (VIB) is prepared and then reacted in-situ with the compound of formula (VIA).

For compounds of formula (I) wherein $R^0$ represents 2-benzoxazolyl, a suitable compound of formula (VIA) is 4-[2-[N-(2-benzoxazolyl)-N-methylamino]ethoxy]benzaldehyde.

A suitable means for separating any required single isomer from a mixture of diastereoisomers is chromatography, such as preparative high pressure liquid chromatography or silica gel column chromatography.

One convenient method for preparing a compound of formula (II) wherein $L^1$ is a $C_{1-6}$ alkoxy group is the basic alcoholysis of a compound of formula (II) wherein $L^1$ is a moiety of formula (b).

A suitable base is an alkali metal alkoxide, for example when $L^1$ is methoxy the compound of formula (II) wherein $L^1$ is moiety (b) is treated with sodium methoxide in methanol.

A compound of formula (I) may also be prepared by resolving a racemic compound of formula (VII):

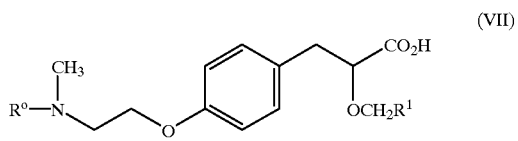

(VII)

wherein $R^0$ and RI are as defined in relation to formula (1); and thereafter, if required, preparing a pharmaceutically acceptable salt of the compound of formula (I) and/or a pharmaceutically acceptable solvate thereof.

The resolution of a compound of formula (VII) may be carried out using known resolution procedures, for example by reacting the compound of formula (VII) with a resolving agent, such as an optically active acid or base, to provide a mixture of diastereoisomeric salts which may then be separated by fractional crystallisation and thereafter the compound of formula (I) may be regenerated from the separated diastereoisomer salt by conventional means, such as hydrolysis.

It will be appreciated that the compounds of formula (VII) comprise the compounds of formula (I) admixed with other optical isomers. A compound of formula (VII) or a pharmaceutically acceptable salt thereof and/or a pharmaceutically acceptable solvate thereof, forms a further aspect of the present invention. The separated isomers of the compounds of formula (VII), in addition to the compounds of formula (I), or a pharmaceutically acceptable salt thereof and/or a pharmaceutically acceptable solvate thereof, also comprise the present invention.

Suitable acids or bases for resolving the compounds of formula (VII) are as described in Enantiomers, Racemates and Resolution, J Jaques et al, 1981, Wiley Interscience, especially at pages 255 and 256. Suitable methods for effecting the resolution are also disclosed by Jaques et al.

The compounds of formula (IV) and (VIA), for example 4-[2-[N-(2-benzoxazolyl)-N-methylamino]ethoxy]benzaldehyde, are known compounds or they may be prepared using methods analogous to those used to prepare known compounds, for example those disclosed in International Patent Application, Publication Number WO94/01420.

The compounds of formula (VIB) are known compounds or they may be prepared using methods analogous to those used to prepare known compounds, for example those disclosed in Organic Synthesis Vol. 68, p83, 1990 Ed. J. D. White or methods analogous thereto, in combination with conventional methodology for the preparation of acid chlorides.

It will be appreciated that in any of the abovementioned reactions any reactive group in the substrate molecule may be protected, according to conventional chemical practice. Suitable protecting groups in any of the abovementioned reactions are those used conventionally in the art. The methods of formation and removal of such protecting groups are those conventional methods appropriate to the molecule being protected.

It will be appreciated that the above mentioned preparation of the compounds of formula (I), or a pharmaceutically acceptable salt thereof and/or a pharmaceutically acceptable solvate thereof, is a stereoselective procedure and that the compound of formula (I) is a single stereoisomer. Favourably a compound of formula (I) is present in admixture with less than 50% w/w of its racemic isomer, that is when it is greater than 50% optically pure, suitably 80–100% and preferably 90–100% pure, such as 90–95%, most preferably 95–100%, for example 95%, 96%, 97%, 98%, 99% or 99.9% optically pure.

Preferably the compound of formula (I) or a pharmaceutically acceptable salt thereof and/or a pharmaceutically acceptable solvate thereof, is in optically pure form.

The absolute stereochemistry of compounds may be determined using conventional methods, such as X-ray crystallography.

When the agonist of PPARα and PPARγ is provided by the combination of a PPARα agonist compound and a PPARγ agonist compound, a suitable PPARγ agonist compound is selected from EP 0306228 and WO94/05659, the contents of which are incorporated herein by reference.

Suitable, favoured and preferred PPARγ agonists are those suitable, favoured and preferred compounds disclosed in EP 0306228 and WO94/05659.

A most preferred PPARγ agonist from EP 0306228 and WO94/05659 is 5-[4-[2-(N-methyl-N-(2-pyridyl)amino)ethoxy]benzyl]thiazolidine-2,4-dione or a tautomeric form thereof and/or a pharmaceutically acceptable salt thereof, especially a maleic acid salt thereof, and/or a pharmaceutically acceptable solvate thereof.

Additional PPARγ agonists include the thiazolidinediones disclosed in European Patent Applications, Publication Numbers:0008203, 0139421, 0032128, 0428312, 0489663, 0155845, 0257781, 0208420, 0177353, 0319189, 0332331, 0332332, 0528734 and 0508740; and from International Patent Application, Publication Numbers 92/18501, 93/02079, 93/22445 and from U.S. Pat. No. 5,104,888; the contents of these publications are also included herein by reference.

When the agonist of PPARα and PPARγ is provided by the combination of a PPARα agonist compound and a PPARγ agonist compound, suitable PPARα agonist are the fibrates such as clofibrate, ciprofibrate, Wy 14643 and BR-931 (Lalwani et al, Biochemical and Biophysical Research commun., Vol. 116, 388–393, 1983); the contents of these publications are included herein by reference. The said fibrates are known compounds prepared using known methodology or analogous methodology to that use to prepare known, analogous compounds, for example the method of d'Atri et al J. Med. Chem., Vol 27, 1621–1629, 1984 is generally applicable to each of the mentioned fibrates.

Also specifically included in the method of the invention are the specific examples disclosed in the above mentioned publications including the patent applications.

The active compounds disclosed in the above mentioned published patent publications, including the specific examples disclosed therein, are conveniently prepared according to the methods disclosed in the said patent publications: For example a PPARγ agonist selected from EP 0306228 or WO94/05659 can be prepared using the processes described in EP 0306228 and WO94/05659.

When used herein 'Syndrome X' includes pre-diabetic insulin resistance syndrome and the resulting complications thereof, insulin resistance, non-insulin dependent diabetes, dyslipidaemia, hyperglycaemia, obesity and the complications associated with diabetes; the methods and treatments mentioned herein include the above unless specifically stated otherwise.

For the avoidance of doubt, the methods and treatments of this invention also encompass the treatment and/or prophylaxis of any one of or any combination of the following list: pre-diabetic insulin resistance syndrome, the resulting complications thereof, insulin resistance, non-insulin dependent diabetes, dyslipidaemia, hyperglycaemia, obesity and the complications associated with diabetes.

The complications associated with diabetes include cardiovascular disease, especially atherosclerosis, retinopathy, neuropathy and renal disease including diabetic nephropathy, glomerulonephritis, glomerular sclerosis, nephrotic syndrome, hypertensive nephrosclerosis and end stage renal disease.

When used herein the term 'PPARα agonist' relates to an agonist of the peroxisomal proliferator-activated receptor, suitably the human receptor, of the alpha subtype.

When used herein the term 'PPARγ agonist' relates to an agonist of the peroxisomal proliferator-activated receptor, suitably the human receptor, of the gamma subtype.

PPARα and γ agonist activity may be assessed by use of the methodology, or similar methodology, to that disclosed by Lehmann et al: Journal of Biological Chem., 270, 12953–12956 (1995).

In one aspect PPARα agonist compounds are those which stimulate a PPAR alpha chimeric receptor consisting of the PPAR alpha ligand binding site linked to a suitable reporter gene construct such as luciferase or chloramphenicol acetyltransferase (CAT). This activity can be identified by using the methods outlined by Lehmann et al., ibid.

In one aspect PPARγ agonist compounds are those which stimulate a PPARγ chimeric receptor containing the PPAR gamma ligand binding site linked to a suitable reporter gene construct such as luciferase or chloramphenicol acetyltransferase (CAT). This activity can be identified by using the methods of Lehmann et al. J Biol. Chem., ibid.

Agonists may be proteins or non-proteins.

Suitable agonists are small molecular weight, non-protein compounds.

Also included in the present invention is a method for detecting a compound having both PPARα and PPARγ agonist activity.

Suitable methods of detection include determining:
(a) PPARα agonist activity by detecting stimulation of a PPAR alpha chimeric receptor consisting of the PPAR alpha ligand binding site linked to a suitable reporter gene construct; and
(b) PPARγ agonist activity by detecting stimulation of a PPARγ chimeric receptor containing the PPAR gamma ligand binding site linked to a suitable reporter gene construct such as luciferase or chloramphenicol acetyltransferase (CAT).

A suitable PPARα chimeric receptor comprises the amino acids of the ligand binding domain, for example amino acids 281–468, of the human PPARα, fused to amino acids 1–147 (DNA binding domain) of the gal 4 yeast transcription factor.

A suitable PPARγ chimeric receptor comprises the amino acids of the ligand binding domain, for example amino acids 173–476, of the human PPARγ receptor fused to amino acids 1–147 (DNA binding domain) of the gal 4 yeast transcription factor.

A suitable reporter gene construct is a luciferase or chloramphenicol acetyltransferase (CAT).

A suitable luciferase reporter gene construct contains gal 4 DNA binding elements in HEK-293 cells.

Suitable methodology for the said method of detection is as described above.

The present invention also provides an agonist of PPARα and PPARγ, for use in the treatment and/or prophylaxis of Syndrome X.

A particular treatment is the prophylaxis of hyperglycaemia.

A particular treatment is the treatment of pre-diabetic insulin resistance syndrome and the resulting complications thereof.

Also included is the treatment and/or prophylaxis of hyperglycaemia and/or pre-diabetic insulin resistance syndrome and the resulting complications thereof; providing the said treatment does not include administration of:
(S)-3-[4-[2-[N-(2-benzoxazolyl)-N-methylamino]ethoxy] phenyl]-2-(2-methoxyethoxy)propanoic acid; or
(S)-3-[4-[2-[N-(2-benzoxazolyl)-N-methylamino]ethoxy] phenyl]-2-(2,2,2-trifluoroethoxy)propanoic acid, for the treatment and/or prophylaxis of: hyperglycaemia, especially in Type II diabetes, hyperlipidaemia, hypertension, cardiovascular disease, especially atherosclerosis and of renal disease, especially renal disease associated with the development of Type II diabetes including diabetic nephropathy, glomerulonephritis, glomerular sclerosis, nephrotic syndrome, hypertensive nephrosclerosis and end stage renal disease and for the prevention, reversal, stabilisation or retardation of the progression of microalbuminuria to albuminuria.

The present invention also provides an agonist of PPARα and PPARγ, for use in the manufacture of a medicament the treatment and/or prophylaxis of Syndrome X, and in particular for the treatment and/or prophylaxis of hyperglycaemia and/or pre-diabetic insulin resistance syndrome and the resulting complications thereof; providing the said treatment does not include administration of:
(S)-3-[4-[2-[N-(2-benzoxazolyl)-N-methylamino]ethoxy] phenyl]-2-(2-methoxyethoxy)propanoic acid; or
(S)-3-[4- [2-[N-(2-benzoxazolyl)-N-methylamino]ethoxy] phenyl]-2-(2,2,2-trifluoroethoxy)propanoic acid, for the treatment and/or prophylaxis of: hyperglycaemia, especially in Type II diabetes, hyperlipidaemia, hypertension, cardiovascular disease, especially atherosclerosis and of renal disease, especially renal disease associated with the development of Type II diabetes including diabetic nephropathy, glomerulonephritis, glomerular sclerosis, nephrotic syndrome, hypertensive nephrosclerosis and end stage renal disease and for the prevention, reversal, stabilisation or retardation of the progression of microalbuminuria to albuminuria.

This is considered to be the first indication of a compound having agonist activity at both PPARα and PPARγ. Other compounds having this dual activity would also be of particular use for the treatment and/or prophylaxis of Syndrome X, including hyperglycaemia and pre-diabetic insulin resistance syndrome and the resulting complications thereof.

Accordingly, in a further aspect the present invention also provides a compound having agonist activity at both PPARα and PPARγ.

Suitable compounds are unique, in that they are not known to have agonist activity at both PPARα and PPARγ or they are novel compounds per se.

In one aspect the said compound having agonist activity at both PPARα and PPARγ does not include:
(S)-3-[4-[2-[N-(2-benzoxazolyl)-N-methylamino]ethoxy] phenyl]-2-(2-methoxyethoxy)propanoic acid; or
(S)-3-[4-[2- [N-(2-benzoxazolyl)-N-methylamino]ethoxy] phenyl]-2-(2,2,2-trifluoroethoxy)propanoic acid.

The invention also provides a compound for use as an agonist of both PPARα and PPARγ.

The invention further provides the a compound having agonist activity at both PPARα and PPARγ for use as an active therapeutic substance; suitably providing that the compound does not include:
(S)-3-[4-[2-[N-(2-benzoxazolyl)-N-methylamino]ethoxy] phenyl]-2-(2-methoxyethoxy)propanoic acid; or
(S)-3-[4-[2-[N-(2-benzoxazolyl)-N-methylamino]ethoxy] phenyl]-2-(2,2,2-trifluoroethoxy)propanoic acid.

In the above mentioned treatments the active compound is administered per se or, preferably, as a pharmaceutical composition also comprising a pharmaceutically acceptable carrier.

Accordingly, the present invention also provides a pharmaceutical composition comprising an agonist of PPARα and PPARγ and a pharmaceutically acceptable carrier therefor; suitably providing the said agonist does not include:
(S)-3-[4-[2-[N-(2-benzoxazolyl)-N-methylamino]ethoxy] phenyl]-2-(2-methoxyethoxy)propanoic acid; or
(S)-3-[4-[2-[N-(2-benzoxazolyl)-N-methylamino]ethoxy] phenyl]-2-(2,2,2-trifluoroethoxy)propanoic acid.

In addition there is provided a method for treating conditions caused by a requirement for an agonist of both PPARα and PPARγ in a human or non-human mammal, which method comprises the administration of an effective, pharmaceutically acceptable, non-toxic amount of an agonist of both PPARα and PPARγ.

As used herein the term 'pharmaceutically acceptable' embraces compounds, compositions and ingredients for both human and veterinary use: for example the term 'pharmaceutically acceptable salt' embraces a veterinarily acceptable salt.

The composition may, if desired, be in the form of a pack accompanied by written or printed instructions for use.

Usually the pharmaceutical compositions of the present invention will be adapted for oral administration, although compositions for administration by other routes, such as by injection and percutaneous absorption are also envisaged.

Particularly suitable compositions for oral administration are unit dosage forms such as tablets and capsules. Other fixed unit dosage forms, such as powders presented in sachets, may also be used.

In accordance with conventional pharmaceutical practice the carrier may comprise a diluent, filler, disintegrant, wetting agent, lubricant, colourant, flavourant or other conventional adjuvant.

Typical carriers include, for example, microcrystalline cellulose, starch, sodium starch glycollate, polyvinylpyrrolidone, polyvinylpolypyrrolidone, magnesium stearate, sodium lauryl sulphate or sucrose.

Most suitably the composition will be formulated in unit dose form. Such unit dose will normally contain an amount of the active ingredient in the range of from 0.1 to 1000 mg, more usually 0.1 to 500 mg, and more especially 0.1 to 250 mg.

Conveniently, the active ingredient may be administered as a pharmaceutical composition hereinbefore defined, and this forms a particular aspect of the present invention.

In the above mentioned treatments the active compounds are suitably taken in doses such as those described above, one to six times a day in a manner such that the total daily dose for a 70 kg adult will generally be in the range of from 0.1 to 6000 mg, and more usually about 1 to 1500 mg, generally about 0.5 to 10 mg. That is in the range of from $1.429 \times 10^{-3}$ to 85.714 mg/kg/day, more usually about $1.429 \times 10^{-2}$ to 21.429 mg/kg/day, generally about $7.143 \times 10^{-3}$ to 0.1429 mg/kg/day.

No adverse toxicological effects are expected when a compound is administered in accordance with the above mentioned invention.

The activity of the present compounds can be demonstrated using the methods disclosed below. The following Preparations illustrate the preparation of the compounds of formula (I).

PREPARATION OF COMPOUNDS OF FORMULA (I)

Preparation 1: (S)-3-[4-[2-[N-(2-Benzoxazolyl)-N-methylamino]ethoxy]phenyl]-2-(2-methoxyethoxy) propanoic acid

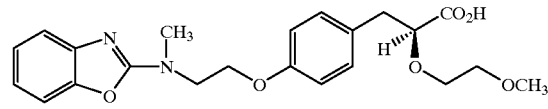

A solution of [2S,N(1S)]-3-[4-[2-[N-(2-benzoxazolyl)-N-methylamino]ethoxy]phenyl]-2-(2-methoxyethoxy)-N-(2-hydroxy-1-phenylethyl)propanamide (1.846 g) in a mixture of 1M sulphuric acid (45 mL) and dioxan/water (1:1, 150 mL) was heated at 90° C. for 56 hours and then the pH of the mixture was adjusted to pH 3 by addition of aqueous sodium hydrogen carbonate. The mixture was extracted with ethyl acetate and the organic extracts washed with water, brine, dried (MgSO$_4$) and evaporated to give an oil. Purification by chromatography on silica gel using a gradient of 1–5% methanol in dichloromethane as eluent gave a foam of 88% e.e. (by HPLC). The product was reacted with (S)-α-methylbenzylamine in acetone, and the resulting salt recrystallised several times from ethyl acetate-hexane before being dissolved in water, acidified with dilute hydrochloric acid and extracted with ethyl acetate which was dried with MgSO$_4$. Evaporation of the ethyl acetate solution afforded enantiomerically enriched title compound; $[\alpha]_D^{25}$ −28° (c=0.625, CHCl$_3$); e.e 94% (by HPLC); [Found M$^+$ 414.1791. C$_{22}$H$_{26}$N$_2$O$_6$ requires M$^+$ 414.1791]; $^1$H NMR spectrum identical with that described in Example 5.

Preparation 2: (S)-3-(4-[2-[N-(2-Benzoxazolyl)-N-methylamino]ethoxy]phenyl]-2-(2,2,2-trifluoroethoxy)propanoic acid by Hydrolysis of Amide

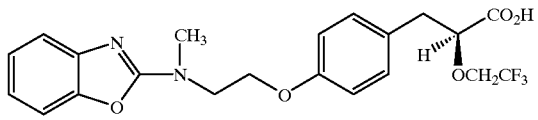

[2S,N(1S)]-3-[4-[2-[N-(2-Benzoxazolyl)-N-methylamino]ethoxy]phenyl]-2-(2,2,2-trifluoroethoxy)-N-(2-hydroxy-1-phenylethyl)propanamide (from Procedure 3) was hydrolysed by an analogous procedure to that described in Preparation 1. Purification by chromatography on silica gel using a gradient of 0–5% methanol in dichloromethane as eluent gave the title compound, mp 116–7° C., after trituration with diethyl ether-hexane; $[\alpha]_D^{25}$ −24.6° (c=0.24, $CHCl_3$); e.e. 95% (by HPLC). [Found C, 57.9; H, 4.7; N, 6.8%; $M^+$ 438.1403. $C_{21}H_{21}F_3N_2O_5$ requires C, 57.5; H, 4.8; N, 6.4%; $M^+$ 438.1403]; $\delta_H$ (DMSO-$d_6$) 2.96 (2H,m), 3.22 (3H,s), 3.88 (2H,m), 3.95–4.18 (2H,m), 4.27 (3H,m), 6.8–7.37 (8H,m) and 12.9 (1H,br s, exchanges with $D_2O$).

Preparation 3: (S)-3-[4-[2-[N-(2-Benzoxazolyl)-N-methylamino]ethoxy]phenyl-2-(2,2,2-trifluoroethoxy)propanoic Acid, by Direct Hydrolysis of the Imide

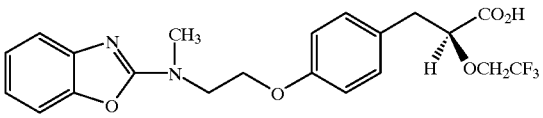

Aqueous sodium hydroxide solution (2.5M, 65 mL, 0.163 mol, 2.3 eq) was added to a stirred solution of [3(2S),4S]-3-[3-[4-[2-[N-(2-benzoxazolyl)-N-methylamino]ethoxy]phenyl]-2-(2,2,2-trifluoroethoxy)propanoyl]-4-benzyloxazolidin-2-one (from Procedure 10)(42.5 g, 0.071 mol) in THF (500 mL) and water (125 mL). The mixture was stirred for 20 minutes, the reaction was diluted with water (1 L) and extracted with dichloromethane (3×700 mL). These dichloromethane solutions were evaporated and the residue purified by chromatography on silica gel using 5% methanol in dichloromethane as eluent to afford (S)-4-benzyloxazolidin-2-one. The original aqueous solution was acidified to pH 3.5 with dilute hydrochloric acid and re-extracted with dichloromethane (3×700 mL). The dichloromethane solutions from the acid extraction were dried ($MgSO_4$) and evaporated to give a solid. This was recrystallised from dichloromethane-diethyl ether to afford the title compound, mp 119.5–120.5° C. $[\alpha]_D^{25}$ −31° (c=2.50, $CHCl_3$); e.e. 99.6% (by HPLC); [Found C, 57.7; H, 4.7; N, 6.25%; $M^+$ (EI) 438.1412. $C_{21}H_{21}F_3N_2O_5$ requires C, 57.5; H, 4.8; N, 6.4%; $M^+$ 438.1403]; $\delta_H$ (CDCl$_3$) 3.05 (1H, dd), 3.13 (1H, dd), 3.31 (3H, s), 3.72 (1H, m), 3.89 (2H, m), 4.04–4.14 (3H, m), 4.21 (1H, dd), 6.78 (2H, d), 7.03–7.40 (6H, m) and 11.20 (1H, br, exchanges with $D_2O$); $\delta_F$ (DMSO-$d_6$)=−72.7 (3F, t, $^3J_{HF}$ 9.3 Hz, $CF_3$).

Preparation 4: (S)-3-[4-[2-[N-(2-Benzoxazolyl)-N-methylamino]ethoxy]phenyl-2-(2,2,2-trifluoroethoxy)propanoic Acid by Hydrolysis of Methyl Ester

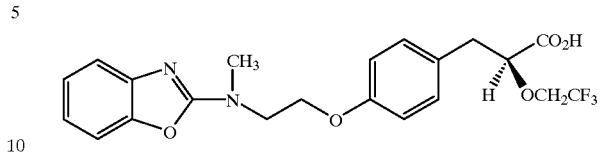

A mixture of (S)-methyl 3-[4-[2-[N-(2-benzoxazolyl)-N-methylamino]ethoxy]phenyl]-2-(2,2,2-trifluoroethoxy) propanoate (1.256 g, 2.8×10$^{-3}$ mol), aqueous hydrochloric acid (2.0M, 50 mL) and dioxan (50 mL) was heated at reflux for 7 hours, cooled and concentrated in vacuo. The residue was suspended in brine (200 mL) and extracted with ethyl acetate (3×300 mL). The combined ethyl acetate solutions were dried ($MgSO_4$) and evaporated to afford a waxy solid. This solid was triturated with hexane, filtered and dried under vacuum at 65° C. to afford the desired product, mp 113–5° C. $[\alpha]_D^{25}$=−32° (c=1.02, $CHCl_3$); e.e. 99.4% (by HPLC); [Found C, 57.25; H, 4.8; N, 6.3%. $C_{21}H_{21}F_3N_2O_5$ requires C, 57.5; H, 4.8; N, 6.4%]. The $^1$H NMR spectrum of this material was identical to that produced in Example 3.

Preparation 5: (S)-3-[4-[2-[N-(2-Benzoxazolyl)-N-methylamino]ethoxy]phenyl-2-(2-methoxyethoxy)propanoic Acid

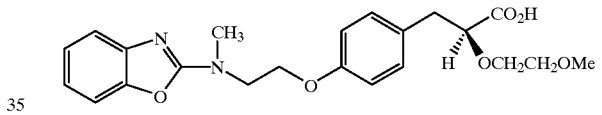

(S)-Methyl 3-[4-[2-[N-(2-benzoxazolyl)-N-methylamino]ethoxy]phenyl]-2-(2-methoxyethoxy) propanoate was hydrolysed in a manner analogous to that described for Example 4. The crude reaction mixture was chromatographed on silica gel using 5% methanol in dichloromethane as eluent to afford the title compound, a gum. $[\alpha]_D^{25}$=−27° (c=0.73, $CHCl_3$); e.e. 99.8% (by HPLC); (Found $M^+$ (EI)414.1779. $C_{22}H_{26}N_2O_6$ requires $M^+$ 414.1791]; $\delta_H$ (CDCl$_3$) 2.90 (1H, dd), 3.15 (1H, dd), 3.33 (3H, s), 3.37 (3H, s), 3.40–3.70 (4H, m), 3.93 (2H, t), 4.05 (1H, dd), 4.21 (2H, t), 6.81 (2H, d) and 6.95–7.40 (6H,m).

Preparation 6: (±)-3-[4-[2-[N-(2-Benzoxazolyl)-N-methylamino]ethoxy]phenyl-2-(2-methoxyethoxy]propanoic acid

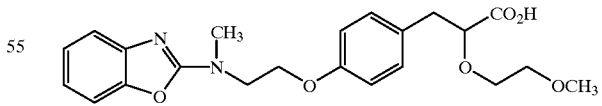

A mixture of methyl 3-[4-[2-[N-(2-benzoxazolyl)-N-methylamino]ethoxy]phenyl]-2-(2-methoxyethoxy) propanoate (1.08 g, Int. Patent Appl., Publication No. WO 9401420) and sodium hydroxide (253 mg) in methanol:water (1:1, 10 mL) was heated under reflux for 2 hours. After evaporation of the resultant mixture in vacuo, the residue was diluted with water, acidified to pH 5 with 2M hydrochloric acid and then extracted with ethyl acetate. Washing of the ethyl acetate extracts with water and drying (MgSO$_4$) and evaporation gave the title compound as an oil which crystallised on trituration with diethyl ether/hexane. [Found C, 63.8; H, 6.5; N, 7.0%; M$^+$ 414.1791. C$_{22}$H$_{26}$N$_2$O$_6$ requires C, 63.8; H, 6.3; N, 6.8%; M$^+$ 414.1791]; $\delta_H$ (CDCl$_3$) 2.91 (1H,dd), 3.15 (1H,dd), 3.34 (3H,s), 3.38 (3H,s), 3.41–3.69 (4H,m), 3.93 (2H,t), 4.05 (1H,dd), 4.21 (2H,t), 6.80 (2H,d) and 6.83–7.38 (6H m).

PROCEDURE 2

Preparation 7: (±)-3-[4-[2-[N-(2-Benzoxazolyl)-N-methylamino]ethoxy]phenyl]-2-(2-methoxyethoxy)propanoyl chloride

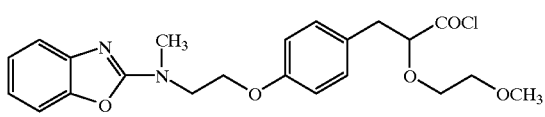

Oxalyl chloride (92 mg) was added to (±)-3-[4-[2-[N-(2-benzoxazolyl)-N-methylamino]ethoxy]phenyl]-2-(2-methoxyethoxy)propanoic acid (100 mg) in dichloromethane (2 mL). The mixture was stirred at room temperature for 16 hours and evaporated to dryness to give the title compound as a gum which was used without further purification.

Preparation 8: [2S,N(1S)]-3-[4-[2-[N-(2-Benzoxazolyl)-N-methylamino]ethoxy]phenyl]-2-(2-methoxyethoxy)-N-(2-hydroxy-1-phenylethyl)propanamide

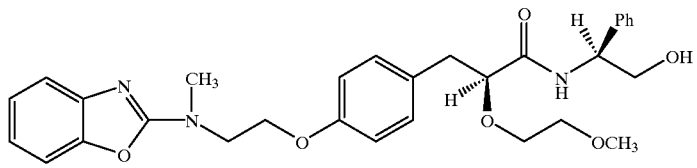

(+)-3-[4-[2-[N-(2-Benzoxazolyl)-N-methylamino]ethoxy]phenyl]-2-(2-methoxyethoxy)propanoyl chloride was dissolved in dichloromethane (2 mL) and a mixture of (S)-2-phenylglycinol (33 mg) and dry triethylamnine (37 mg) in dichloromethane (1 mL) added. After stirring for 5 minutes water was added and the mixture extracted with dichloromethane. The organic extracts were washed with water, brine, dried (MgSO$_4$) and evaporated. The residue was chromatographed on silica gel using a gradient of 10–50% acetone in hexane as eluent to afford firstly [2R,N(1S)]-3-[4-[2-[N-(2-benzoxazolyl)-N-methylamino]ethoxy]phenyl]-2-(2-methoxyethoxy)-N-(2-hydroxy-1-phenylethyl)propanamide followed by the desired [2S,N(1S)]-propanamide title compound as a foam. [α]$_D^{25}$ –33° (c=1.1, CHCl$_3$); 92.6% d.e. (by HPLC); [Found M$^+$ 533.2526. C$_{30}$H$_{35}$N$_3$O$_5$ requires M$^+$ 533.2526]; $\delta_H$ (CDCl$_3$) 2.81 (1H,dd), 3.07 (1H,dd), 3.35 (3H,s), 3.36 (3H,s), 3.48–3.58 (2H,m), 3.52–3.62 (2H,m), 3.71 (1H,dd), 3.82 (1H,dd), 3.94 (1H,dd), 3.93 (2H,t), 4.22 (3H,t), 5.05 (1H,dt), 6.75–7.35 (13H,complex), 7.54 (1H,br, exchanges with D$_2$O).

PROCEDURE 4

Preparation 9: (±)-3-[4-[2-[N-(2-Benzoxazolyl)-N-methylamino]ethoxy]phenyl]-2-(2,2,2-trifluoroethoxy)propanoic acid

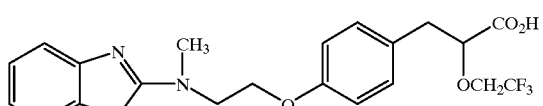

Methyl 3-[4-[2-[N-(2-benzoxazolyl)-N-methylamino]ethoxy]phenyl]-2-(2,2,2-trifluoroethoxy)propanoate (Int. Patent Appl., Publication No. WO 9401420) was hydrolysed by an analogous procedure to that described in Preparation 5 to give the title compound as a solid, mp 116–117° C.; [Found C, 57.4; H, 4.9; N, 6.4%. C$_{21}$H$_{21}$F$_3$N$_2$O$_5$ requires C, 57.5; H, 4.8; N, 6.4%); $\delta_H$ (CDCl$_3$) 3.03–3.17 (2H,m), 3.29 (3H,s), 3.73–3.83 (1H,m), 3.85 (2H,m), 4.02 (2H,m), 4.04–4.30 (2H,m) and 6.74–7.40 (8H m).

PROCEDURE 5

Preparation 10: (±)-3-[4-[2-[N-(2-Benzoxazolyl)-N-methylamino]ethoxy]phenyl]-2-(2,2,2-trifluoroethoxy)propanoyl chloride

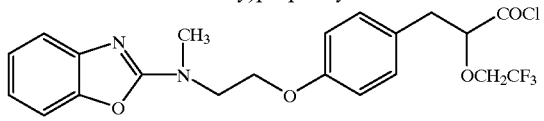

Oxalyl chloride (1.1 mL) was added to a solution of (±)-3-[4-[2-[N-(2-benzoxazolyl)-N-methylamino]ethoxy]phenyl]-2-(2,2,2-trifluoroethoxy)propanoic acid (1.72 g) in dry benzene (30 mL). The mixture was heated at reflux for 2 hours, cooled and evaporated to dryness to give the title compound as a gum which was used without further purification.

PROCEDURE 6

Preparation 11: [2S,N(1S)]-3-[4-[2-[N-(2-Benzoxazolyl)-N-methylamino]ethoxy]phenyl]-2-(2,2,2-trifluoroethoxy)-N-(2-hydroxy-1-phenylethyl)propanamide

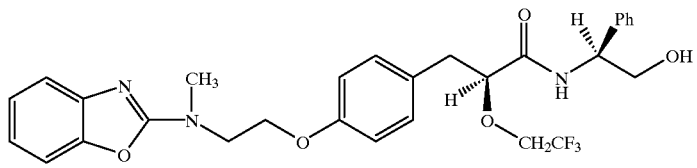

(±)-3-[4-[2-[N-(2-Benzoxazolyl)-N-methylamino]ethoxy]phenyl]-2-(2,2,2-trifluoroethoxy)propanoyl chloride was reacted with (S)-2-phenylglycinol by an analogous procedure to that described in Procedure 3. Chromatography on silica gel using a gradient of 10–70% ethyl acetate in hexane as eluent afforded firstly [2R,N(1S)]-3-[4-[2-[N-(2-benzoxazolyl)-N-methylamino]ethoxy]phenyl]-2-(2,2,2-trifluoroethoxy)-N-(2-hydroxy-1-phenylethyl)propanamide followed by the desired [2S,N(1S)]-propanamide title compound as a foam; $[\alpha]_D^{25}$ +14° (c=0.5, MeOH); 99% d.e. (by HPLC); [Found M+ 557.2136. $C_{29}H_{30}F_3N_3O_5$ requires M+ 557.2138]; $\delta_H$ (CDCl₃) 2.35 (1H,br, exchanges with D₂O), 2.91 (1H,dd), 3.13 (1H,dd), 3.36 (3H,s), 3.70–3.87 (2H,m), 3.84 (2H,d), 3.95 (2H,t), 4.12 (1H,dd), 4.22 (2H,t), 5.01 (1H,m), 6.75 (2H,d), 6.97 (1H,br s, exchanges with D₂O) and 7.01–7.36 (11H,complex).

Preparation 12: (2,2,2-Trifluoroethoxy)ethanoyl Chloride

A solution of oxalyl chloride (20 mL, 0.23 mol, 1.15 eq) in dry dichloromethane (50 mL) was added dropwise at room temperature, with stirring, to a solution of (2,2,2-trifluoroethoxy)ethanoic acid (int. Patent Appl., Publication No. WO 87/07270, 31.6 g, 0.2 mol) and N,N-dimethylformamide (5 drops) in dry dichloromethane (400 mL). The mixture was stirred for an additional hour, then heated under reflux for 2 hours, cooled and the bulk of the solvent removed by distillation (bp 40–45° C./760 mm Hg). The residue was transferred to a Claisen distillation flask and the remaining solvent and oxalyl chloride removed by distillation (bp 45–60° C./760 mm Hg). Vacuum distillation of the residue then afforded the product, bp 50–55°/25–32 mm Hg. $\delta_H$ (CDCl₃) 4.00 (2H, q, $^3J_{HF}$ 8.3) and 4.57 (2H, s).

PROCEDURE 8

Preparation 13: (4S)-4-Benzyl-3-[2-(2,2,2-trifluoroethoxy)ethanoyl]oxazolidin-2-one

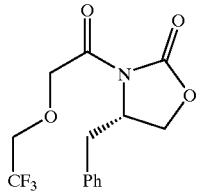

(4S)-4-Benzyloxazolidine-2-one (5.21 g, 0.029 mol) was dissolved in dry THF (60 mL) and cooled to −70° C. under argon. n-Butyllithium (18.4 mL, 1.6 M solution in hexane, 1.1 eq) was added over 10 minutes and the resulting mixture stirred at −70° C. for 20 minutes. A solution of (2,2,2-trifluoroethoxy)ethanoyl chloride (5.19 g, 1 eq) in dry TUF (60 mL) was added over 10 minutes, the mixture stirred at −70° C. for a further 30 minutes then allowed to warm to room temperature overnight. The reaction was quenched by addition of brine (20 mL) and concentrated in vacuo. The residue was diluted with brine (300 mL) and extracted with ethyl acetate (3×300 mL). The combined organic extracts were dried (MgSO₄), evaporated and the residue chromatographed on silica gel with dichloromethane as eluent to give the product as an oil. $[\alpha]_D^{25}$=+48° (c=2.55, CHCl₃); e.e. 100% (by HPLC); [Found (CI, Ammonia) MH+ 318.0934. $C_{14}H_{14}NO_4F_3$ requires MH+ 318.0953]; $\delta_H$ (CDCl₃) 2.82 (1H, dd), 3.34 (1H, dd), 4.02 (2H, q, $^3J_{HF}$ 8.6), 4.30 (2H, m), 4.69 (1H, m), 4.84 (2H, s) and 7.15–7.40 (5H, m); $\delta_F$ (CDCl₃)=−74.8 (3F, t, $^3J_{HF}$ 8.6, CF₃).

PROCEDURE 9

Preparation 14: [3(2S,3R),4S]-3-[3-[4-[2-[N-(2-Benzoxazolyl)-N-methylamino]ethoxy]phenyl]-3-hydroxy-2-(2,2,2-trifluoroethoxy)propanoyl]-4-benzyloxazolidin-2-one

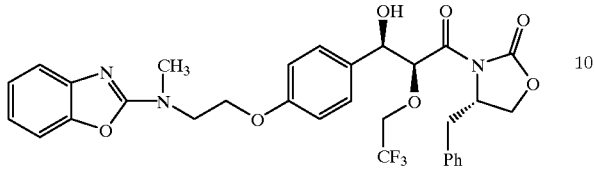

(4S)-4-Benzyl-3-[2-(2,2,2-trifluoroethoxy)ethanoyl]oxazolidin-2-one (31.7 g, 0.1 mol) was dissolved in dry dichloromethane (300 mL) under argon and cooled to −78° C. (internal temperature of solution), using liquid nitrogen/acetone as the cooling medium. Triethylamine (16.72 mL, 1.2 eq) was added, followed by the slow addition, over approximately 10 minutes, of di-n-butylboron triflate (Aldrich Chemical Company, 1.0M solution in dichloromethane, 110 mL, 1.1 eq) such that the reaction temperature was maintained below −70° C. The mixture was stirred at −78° C. for 50 minutes, then the cooling bath was replaced with an ice bath and the mixture stirred at 0° C. for an additional 50 minutes before being recooled to −78° C. A solution of 4-[2-[N-(2-benzoxazolyl)-N-methylamino]ethoxy]benzaldehyde (29.6 g, 1.0 eq) in dry dichloromethane (220 mL), precooled to −50° C., was added over ca. 12 minutes, such that the reaction temperature was maintained below −70° C. The resulting mixture was stirred at −78° C. for 30 minutes, then warmed from −78° C. to 0° C. over 60 minutes along a linear gradient (warming rate ~1.3° C. min$^{-1}$) and stirred at 0° C. for a further 75 minutes. The reaction mixture was poured into a quenching solution of methanol (500 mL), pH 7 phosphate buffer (250 mL) and hydrogen peroxide (27.5% w/v, 110 mL) and stirred vigourously for 30 minutes. Water (4 L) was added, the layers were separated and the aqueous layer was extracted with dichloromethane (3×1 L). The dichloromethane solutions were recombined with the original dichloromethane layer from the reaction mixture and this organic solution was then washed with water (2 L) and brine (2 L), dried (MgSO$_4$) and evaporated to afford a foam. $^1$H NMR of this crude reaction mixture suggested a mixture of the desired aldol product (3 diastereoisomers, comprising 95% major diastereoisomer) and starting materials. The crude mixture was chromatographed on silica gel using a gradient elution comprising 15% ethyl acetate in dichloromethane initially (until the desired product began to elute) and rising to 50% ethyl acetate in dichloromethane to complete the elution of the desired product. Unreacted imide and aldehyde were recovered from the early fractions, followed by a quantity of impure product and then the title compound (comprising 2 diastereoisomers, ratio 97.8:2.2 by NMR). [α]$_D^{25}$=+45° (c=2.82, CHCl$_3$). [Found (EI) M$^+$ 613.2042. C$_{31}$H$_{30}$F$_3$N$_3$O$_7$ requires M$^+$ 613.2036]; δ$_H$ (CDCl$_3$, only major diastereoisomer is recorded) 2.75 (1H, dd), 2.90 (1H, d, exchanges with D$_2$O), 3.25 (1H, dd), 3.34 (3H, s), 3.80–4.00 (5H, m), 4.07 (1H, dd), 4.24 (2H, t), 4.45 (1H, m), 4.99 (1H, apparent t), 5.48 (1H, d), 6.85 (2H, d) and 6.95–7.40 (11H, m); δ$_F$ (CDCl$_3$)=−74.7 (3F, t, $^3$J$_{HF}$ 8.5, CF$_3$). The minor diastereoisomer in the purified product was identified as the [3(2S,3S),4S]-diastereoisomer.

PROCEDURE 10

Preparation 15: [3(2S),4S]-3-[3-[4-[2-[N-(2-Benzoxazolyl)-N-methylamino]ethoxy]phenyl]-2-(2,2,2-trifluoroethoxy)propanoyl]-4-benzyloxazolidin-2-one by Dehydroxylation

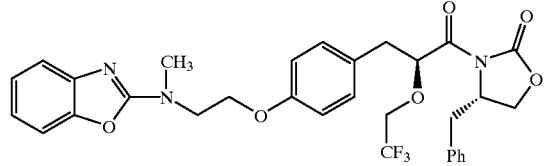

Triethylsilane (120 mL, 0.75 mol) was added over 5 minutes to a stirred, ice cooled solution of [3(2S,3R),4S]-3-[3-[4-[2-[N-(2-benzoxazolyl)-N-methylamino]ethoxy]phenyl]-3-hydroxy-2-(2,2,2-trifluoroethoxy)propanoyl]-4-benzyloxazolidin-2-one (46.23 g, 7.5×10$^{-2}$ mol) in trifluoroacetic acid (650 mL). The mixture was stirred at 0° C. for 1 hour, then at room temperature for a further 60 hours. The bulk of the solvent and residual triethylsilane was removed by rotary evaporation, firstly at 40 mm Hg and finally at ~5 mm Hg. The residue was dissolved in dichloromethane (800 mL) and water (800 mL), then stirred vigorously during the cautious addition of solid sodium bicarbonate (~29 g) (frothing !) until the pH of the aqueous layer was pH 7. The layers were separated and the aqueous layer was extracted with dichloromethane (800 mL). The combined dichloromethane layers were washed with water (600 mL), dried (MgSO$_4$) and evaporated. The residue was triturated with hot hexane and the resulting solid collected by filtration. Recrystallisation from diethyl ether-hexane afforded the title compound, mp 107–109° C., a single diastereoisomer by $^1$H NMR spectroscopy. [α]$_D^{25}$=+38° (c=1.51, CHCl$_3$); [Found C, 62.1; H, 4.9; N, 7.2%; M$^+$ (EI) 597.2089. C$_{31}$H$_{30}$N$_3$O$_6$F$_3$ requires C, 62.3; H, 5.1; N, 7.0%; M$^+$ 597.2087]; δ$_H$ (CDCl$_3$) 2.82 (1H, dd), 2.96 (1H, dd), 3.04 (1H, dd), 3.32 (1H, dd), 3.34 (3H, s), 3.70 (1H, m), 3.88 (1H, m), 3.94 (2H, t), 4.12 (1H, m), 4.18 (1H, m), 4.25 (2H, t), 4.57 (1H, m), 5.34 (1H, dd), 6.82 (2H, d) and 7.00–7.35 (11H, m); δ$_F$ (CDCl$_3$)=−74.8 (3F, t, $^3$J$_{HF}$ 8.6, CF$_3$).

PROCEDURE 11

Preparation 16: [3(2S),4S]-3-[3-[4-[2-[N-(2-Benzoxazolyl)-N-methylamino]ethoxy]phenyl]-2-(2,2,2-trifluoroethoxy)propanoyl]-4-benzyloxazolidin-2-one via Diastereoisomer Separation

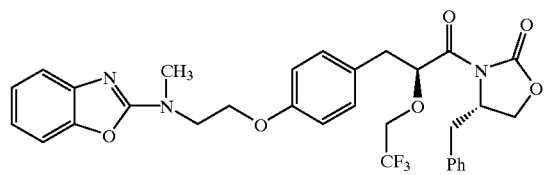

(S)-4-Benzyloxazolidin-2-one (0.291 g, 1.64×10$^{-3}$ mol) was dissolved in dry THF (10 mL) and the resulting solution cooled to −70° C. under argon. n-Butyl lithium (1.6M in hexane, 1.03 mL, 1.64×10$^{-3}$ mol) was added and the mixture was stirred at −70° C. for 10 minutes prior to the addition of a solution of (±)-3-[4-[2-[N-(2-benzoxazolyl)-N-methylamino]ethoxy]phenyl]-2-(2,2,2-trifluoroethoxy)

propanoyl chloride (prepared from 0.36 g of the acid by Procedure 5, above) in dry THF (15 mL). The reaction was stirred and allowed to warm to room temperature overnight before being diluted with water (200 mL) and extracted with ethyl acetate (2×200 mL). The combined ethyl acetate layers were washed with water (200 mL) and brine (200 mL), dried (MgSO$_4$) and evaporated to give a brown gum. This was chromatographed on silica gel using a gradient of 35% to 50% ethyl acetate in hexane as eluent to afford firstly the (R,S)-diastereoisomer, followed by the title compound, a foam. This material was spectroscopically identical with that prepared by the aldol route (Procedure 10).

PROCEDURE 12

Preparation 17: (S)-Methyl 3-[4-[2-[N-(2-Benzoxazolyl)-N-methylamino]ethoxy]phenyl]-2-(2,2,2-trifluoroethoxy)propanoate

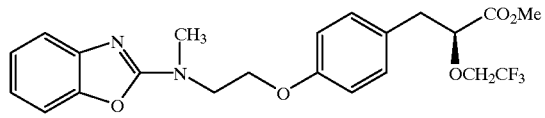

A solution of sodium methoxide [prepared from sodium hydride (60% dispersion in mineral oil, 138 mg, 3.41×10$^{-3}$ mol) dissolved in dry methanol (3.5 mL)] was added to an ice cooled and stirred suspension of [3(2S),4S]-3-[3-[4-[2-[N-(2-benzoxazolyl)-N-methylamino]ethoxy]phenyl]-2-(2,2,2-trifluoroethoxy)propanoyl]-4-benzyloxazolidin-2-one (1.879 g, 3.1×10$^{-3}$ mol) in dry methanol (100 mL). The mixture was stirred at 0° C. for a total of 20 minutes, then the reaction was quenched by the addition of dilute aqueous hydrochloric acid (2.0M, 1.75 mL) and concentrated in vacuo. The residue was suspended in water (100 mL), extracted with ethyl acetate (3×200 mL) and the combined ethyl acetate solutions washed with brine (500 mL), dried (MgSO$_4$) and evaporated. The resulting gum was chromatographed on silica gel using 4% ethyl acetate in dichloromethane as eluent to afford the product as a clear gum. $[\alpha]_D^{25}$=−17° (c=1.24, CHCl$_3$); [Found (EI) M$^+$ 452.1561. C$_{22}$H$_{23}$N$_2$O$_5$F$_3$ requires M$^+$ 452.1559]; e.e. 100% (by HPLC); $\delta_H$ (CDCl$_3$) 3.02 (2H, m), 3.34 (3H, s), 3.65 (1H, m), 3.72 (3H, s), 3.94 (2H, t), 4.00 (1H, m), 4.13 (1H, dd), 4.24 (2H, t), 6.80 (2H, d) and 6.96–7.40 (6H, m).

PROCEDURE 13

Preparation 18: (4S)-4-Benzyl-3-[2-(2-methoxyethoxy)ethanoyl]oxazolidin-2-one

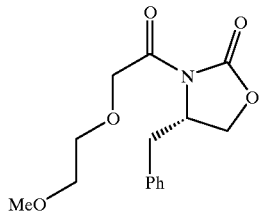

The title compound was prepared from 2-(2-methoxyethoxy)ethanoyl chloride by a method analogous to that described in Procedure 8. Chromatography on silica gel using a gradient of 70–80% diethyl ether in hexane as eluent afforded the product as a gum. $[\alpha]_D^{25}$=+54° (c=2.70, CHCl$_3$); [Found (EI) M$^+$ 293.1263. C$_{15}$H$_{19}$NO$_5$ requires M$^+$ 293.1264]; $\delta_H$ (CDCl$_3$) 2.81 (1H, dd), 3.33 (1H, dd), 3.41 (3H, s), 3.63 (2H, t), 3.78 (2H, t), 4.25 (2H, m), 4.70 (1H, m), 4.74 (1H, d), 4.76 (1H, d) and 7.10–7.40 (5H, m).

PROCEDURE 14

Preparation 19: [3(2S,3R),4S]-3-[3-[4-[2-[N-(2-Benzoxazolyl)-N-methylamino]ethoxy]phenyl]-3-hydroxy-2-(2-methoxyethoxy)propanoyl]-4-benzyloxazolidin-2-one

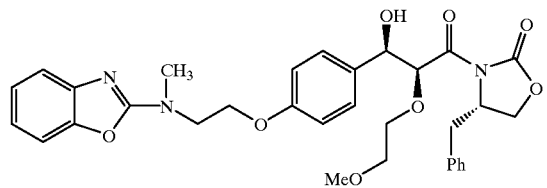

The title compound was prepared from (4S)-4-benzyl-3-[2-(2-methoxyethoxy)ethanoyl]oxazolidin-2-one by a method analogous to that described in Procedure 9. The crude reaction mixture was chromatographed on silica gel using a gradient of 15–40% ethyl acetate in dichloromethane to afford the product as a gum (comprising 2 diastereoisomers, ratio >99:1 by $^1$H NMR). $[\alpha]_D^{25}$=+49° (c=1.14, CHCl$_3$). [Found (FAB, NOBA/Na) MH$^+$ 590.2472. C$_{32}$H$_{35}$N$_3$O$_8$ requires MH$^+$ 590.2502]; $\delta_H$ (CDCl$_3$, only major diastereoisomer is recorded) 2.71 (1H, dd), 3.25 (1H, dd), 3.31 (3H, s), 3.35 (3H, s), 3.56 (2H, m), 3.72 (2H, m), 3.78 (1H, d, exchanges with D$_2$O), 3.85–4.00 (4H, m), 4.22 (2H, t), 4.31 (1H, m), 4.89 (1H, dd), 5.42 (1H, d), 6.83 (2H, d) and 6.95–7.40 (11H, m); The minor diastereoisomer in the purified product was identified as the [3(2S,3S),4S]-diastereoisomer.

PROCEDURE 15

Preparation 20: [3(2S),4S]-3-[3-[4-[2-[N-(2-Benzoxazolyl)-N-methylamino]ethoxy]phenyl]-2-(2-methoxyethoxy)propanoyl]-4-benzyloxazolidin-2-one

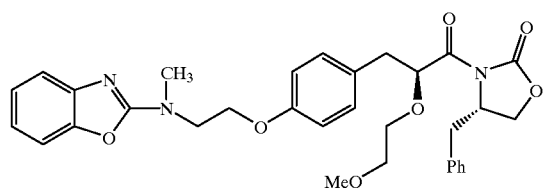

[3(2S,3R),4S]-3-[3-[4-[2-IN-(2-benzoxazolyl)-N-methylamino]ethoxy]phenyl]-3-hydroxy-2-(2-methoxyethoxy)propanoyl]-4-benzyloxazolidin-2-one (0.561 g) was reacted with triethylsilane for 6.25 hrs in a manner similar to that described for Procedure 10. The reaction mixture was diluted with water (200 mL) and dichloromethane (200 mL) and solid sodium bicarbonate was added cautiously until the aqueous layer showed pH 6.5. The layers were separated, the aqueous layer was extracted with dichloromethane (2×300 mL) and the combined dichloromethane solutions were washed with brine (400 mL), dried (MgSO$_4$) and evaporated. The residue was chromatographed on silica gel using 35% ethyl acetate in dichloromethane as eluent to afford the title compound, a gum, as a single diastereoisomer by $^1$H NMR. $[\alpha]_D^{25}$=+45° (c=1.39, CHCl$_3$); [Found M$^+$ (EI) 573.2473. C$_{32}$H$_{35}$N$_3$O$_7$ requires M$^+$ 573.2475]; $\delta_H$(CDCl$_3$) 2.76 (1H, dd), 2.94 (2H, m), 3.30 (3H, s), 3.33 (4H, m), 3.40–3.70 (4H, m), 3.93 (2H, t), 4.00 (1H, dd), 4.12 (1H, dd), 4.22 (2H, t), 4.52 (1H, m), 5.31 (1H, dd), 6.79 (2H, d) and 6.90–7.40 (11H, m).

PROCEDURE 16

Preparation 21: (S)-Methyl 3-[4-[2-[N-(2-Benzoxazolyl)-N-methylamino]ethoxy]phenyl]-2-(2-methoxyethoxy)propanoate

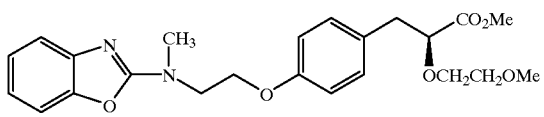

[3(2S),4S]-3-[3-[4-[2-[N-(2-benzoxazolyl)-N-methylamino]ethoxy]phenyl]-2-(Z2-methoxyethoxy)propanoyl]-4-benzyloxazolidin-2-one was reacted with sodium methoxide in a manner analogous to that described in Procedure 12. The crude reaction mixture was chromatographed on silica gel using 20% isohexane in diethyl ether as eluent to afford the title compound, a gum. $[\alpha]_D^{25}$=−12° (c=1.26, CHCl$_3$); [Found (EI) M$^+$ 428.1974. C$_{23}$H$_{28}$N$_2$O$_6$ requires M$^+$ 428.1948]; e.e. >99.8% (by HPLC); $\delta_H$(CDCl$_3$) 2.95 (2H, m), 3.29 (3H, s), 3.34 (3H, s), 3.35 (3H, m), 3.69 (4H, m), 3.93 (2H, t), 4.05 (1H, dd), 4.23 (2H, t) and 6.75–7.40 (8H, m).

Demonstration of Efficacy of Compounds

1) Determination of hPPARα and hPPAR-γ Agonist Activity

Compound agonist effects at human PPARα and PPARγ were assessed using a transactivation reporter gene assay, based on that described by Lehman et al. (1995) J Biol Chem 270, 12953–12956.

Results: Efficacy of (S)-3-[4-[2-[N-(2-Benzoxazolyl)-N-methylamino]ethoxy]phenyl]2-(2,2,2-trifluoroethoxy) propanoic acid at hPPARα and hPPARγ
EC$_{50}$ for activation of human PPARα is=2500 nM
EC$_{50}$ for activation of human PPARγ is=70 nM 2) Determination of Compound Efficacy on Blood Glucose and Plasma Lipids in the C57 Bl/KsJ db/db Mouse The genetically diabetic C57 Bl/KsJ db/db mouse displays a severe form of non insulin dependent diabetes mellitus in that it develops a profound hyperglycaemia at about 8 weeks of age. This is paralleled by glycosuria and polyuria with a compensatory increase in water intake. Circulating serum triglycerides and free fatty acids are also elevated.

Compounds are administered by dietary admixture (powdered RM3 diet) for 14 days and blood glucose measured in samples taken from the tail vein of conscious non-fasted mice at appropriate intervals during the treatment period. After the 14 day treatment period, mice are killed by cervical dislocation and blood obtained from the severed jugular veins. Triglyceride and non-esterified fatty acids are measured in samples of serum obtained by centrifugation.

Efficacy of (S)-3-[4-[2-[N-(2-Benzoxazolyl)-N-methylamino]ethoxy]phenyl]2-(2,2,2-trifluoroethoxy)propanoic acid on Blood Glucose in the Diabetic Mouse

|  |  | Control | Treated |
|---|---|---|---|
| EXPT I | Blood glucose (mmol/l) | | |
|  | pre-dose | 15.5 ± 3.7 | 15.6 ± 4.0 |
|  | post dose (13 days) | 34.0 ± 7.9 | ***11.0 ± 3.6 |
|  | Blood glucose (mmo/l) | | |
|  | pre-dose | 16.5 ± 2.9 | 16.2 ± 4.3 |
|  | Day 1 | 17.2 ± 3.7 | 14.1 ± 3.7 |
| EXPTII | Day 2 | 19.9 ± 2.7 | **15.0 ± 3.4 |
|  | Day 3 | 20.2 ± 3.9 | ***12.2 ± 5.1 |
|  | Day 5 | 21.2 ± 1.9 | ***11.3 ± 3.6 |
|  | Day 7 | 23.4 ± 2.0 | ***11.7 ± 3.7 |

Results are mean ± SD (n = 9–10 per group).  p < 0.01; * p < 0.001 vs controls.

Effect of (S)-3-[4-[2-[N-(2-Benzoxazolyl)-Nmethylamino]ethoxy]phenyl]2-(2,2,2-trifluoroethoxy)propanoic acid on Serum Lipids in the Genetically Diabetic Mouse

| Parameter | Control | Treated (0.3 umol/kg body wt) |
|---|---|---|
| Serum non-esterified fatty acids (mmol/l) | 2.58 ± 0.45 | ***1.28 ± 0.15 |
| Serum triglycerides (mmol/l) | 3.78 ± 1.34 | ***2.58 ± 0.45 |

Parameters were measured in samples taken after 14 days of treatment (dietary admixture). Values are mean ± SD (n ± 9). *** p < 0.001 versus controls.

What is claimed is:

1. A method for the treatment or prophylaxis of Syndrome X in a human or non-human mammal, which method comprises the administration of an effective, non-toxic and pharmaceutically effective amount of an agonist of PPARα and PPARγ, or a pharmaceutically acceptable derivative thereof, to a human or non-human mammal in need thereof.

2. A method according to claim 1, wherein the agonist of PPARα and PPARγ is the same compound.

3. A method according to claim 1 for the treatment or prophylaxis of hyperglycemia.

4. A method according to claim 1, for the treatment of pre-diabetic insulin resistance syndrome and the resulting complications thereof.

5. A method according to claim 1, wherein the PPARα and γ agonist is a compound of formula (I):

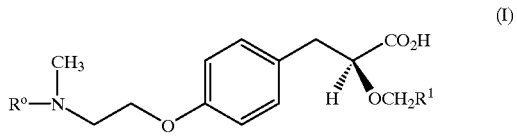

or a pharmaceutically acceptable salt thereof, and/or a pharmaceutically acceptable solvate thereof, wherein R$^0$ represents 2-benzoxazolyl or 2-pyridyl and R$^1$ represents CH$_2$OCH$_3$ or CF$_3$.

* * * * *